United States Patent
Helf et al.

(10) Patent No.: US 9,089,622 B2
(45) Date of Patent: Jul. 28, 2015

(54) VOLATILE MATERIAL DISPENSER

(71) Applicant: S.C. Johnson & Son, Inc., Racine, WI (US)

(72) Inventors: Thomas A. Helf, New Berlin, WI (US); Edward L. Paas, Los Altos, CA (US)

(73) Assignee: S.C. Johnson & Son, Inc., Racine, WI (US)

( * ) Notice: Subject to any disclaimer, the term of this patent is extended or adjusted under 35 U.S.C. 154(b) by 10 days.

(21) Appl. No.: 13/748,293

(22) Filed: Jan. 23, 2013

(65) Prior Publication Data

US 2013/0161348 A1    Jun. 27, 2013

Related U.S. Application Data

(62) Division of application No. 12/054,054, filed on Mar. 24, 2008, now Pat. No. 8,387,827.

(51) Int. Cl.

| | |
|---|---|
| *B67D 1/00* | (2006.01) |
| *A61L 9/14* | (2006.01) |
| *B65D 83/26* | (2006.01) |
| *A01M 1/20* | (2006.01) |
| *B65D 83/14* | (2006.01) |
| *B05B 15/06* | (2006.01) |
| *B65D 83/46* | (2006.01) |

(52) U.S. Cl.
CPC ............... *A61L 9/14* (2013.01); *A01M 1/2038* (2013.01); *B65D 83/26* (2013.01); *B65D 83/262* (2013.01); *B65D 83/753* (2013.01); *B05B 15/066* (2013.01); *B65D 83/46* (2013.01)

(58) Field of Classification Search
USPC .............. 222/52, 63, 333, 504, 402.21, 527, 222/383.1, 383.3, 321.1, 321.7–321.9, 222/402.13
See application file for complete search history.

(56) References Cited

U.S. PATENT DOCUMENTS

| | | |
|---|---|---|
| 2,506,449 A | 11/1946 | Greenwood |
| 2,662,669 A | 1/1950 | Schmidt |
| 2,763,406 A | 6/1952 | Countryman |
| 2,608,319 A | 8/1952 | Petry |
| 2,613,108 A | 10/1952 | Kraus |
| 2,912,144 A | 9/1956 | Luddecke |
| 2,948,439 A | 11/1956 | Glover |
| 2,868,419 A | 12/1956 | Casey, Jr. |
| 3,018,929 A | 9/1959 | Obst |

(Continued)

FOREIGN PATENT DOCUMENTS

| | | |
|---|---|---|
| EP | 656230 | 6/1995 |
| EP | 0676133 | 10/1995 |

(Continued)

OTHER PUBLICATIONS

International Search Report and Written Opinion dated Dec. 29, 2009 Appl. No. PCT/US2009/001836.

(Continued)

*Primary Examiner* — Donnell Long

(57) ABSTRACT

A volatile material dispenser includes a drive unit adapted to be mounted on a container. The drive unit is adapted to be activated in response to a signal from at least a sensor to radially displace a tilt-activated valve stem of the container. The volatile material dispenser further includes a flexible tube having a discharge end fixedly held with respect to the container. The flexible tube is adapted to be in fluid communication with the tilt-activated valve stem.

6 Claims, 11 Drawing Sheets

(56) References Cited

U.S. PATENT DOCUMENTS

| | | |
|---|---|---|
| 2,928,573 A | 3/1960 | Edelstein |
| 3,018,056 A | 1/1962 | Montgomery |
| 3,023,427 A | 3/1962 | Behringer |
| 3,028,054 A | 4/1962 | Beard, Jr. |
| 3,050,281 A | 8/1962 | Budwig |
| 3,088,682 A | 5/1963 | Venus, Jr. |
| 3,115,277 A | 12/1963 | Montague, Jr. |
| 3,127,060 A | 3/1964 | Vosbikian et al. |
| 3,154,224 A | 10/1964 | Wakeman |
| 3,155,290 A | 11/1964 | Venus, Jr. |
| 3,161,196 A | 12/1964 | Berkow |
| 3,165,238 A | 1/1965 | Wiley |
| 3,178,070 A * | 4/1965 | Leland .......... 222/180 |
| 3,180,532 A | 4/1965 | Michel |
| 3,185,356 A | 5/1965 | Venus, Jr. |
| 3,199,732 A | 8/1965 | Strachen |
| 3,228,609 A | 1/1966 | Edelstein et al. |
| 3,240,389 A | 3/1966 | Genua |
| 3,269,602 A | 8/1966 | Weber, III |
| 3,270,925 A | 9/1966 | Obst |
| 3,273,610 A | 9/1966 | Frost |
| 3,289,886 A | 12/1966 | Goldsholl et al. |
| 3,305,134 A | 2/1967 | Carmichael et al. |
| 3,326,418 A | 6/1967 | Kropp |
| 3,329,314 A | 7/1967 | Kolodziej |
| 3,368,717 A | 2/1968 | Weber, III |
| 3,398,864 A | 8/1968 | Kolodziej |
| 3,411,670 A | 11/1968 | Mangel |
| 3,419,189 A | 12/1968 | Iketani |
| 3,455,485 A | 7/1969 | Crownover |
| 3,477,613 A | 11/1969 | Mangel |
| 3,497,108 A | 2/1970 | Mason |
| 3,497,110 A | 2/1970 | Bombero et al. |
| 3,515,316 A | 6/1970 | Green |
| 3,540,624 A * | 11/1970 | Green .......... 222/108 |
| 3,542,248 A | 11/1970 | Mangel |
| 3,543,122 A | 11/1970 | Klebanoff et al. |
| 3,584,766 A | 6/1971 | Hart et al. |
| 3,589,562 A | 6/1971 | Buck |
| 3,589,563 A | 6/1971 | Carragan et al. |
| 3,591,058 A | 7/1971 | Johnston |
| 3,617,214 A | 11/1971 | Dolac |
| 3,620,023 A | 11/1971 | Schmid |
| 3,627,176 A | 12/1971 | Sailors |
| 3,632,020 A | 1/1972 | Nixon, Jr. et al. |
| 3,643,836 A | 2/1972 | Hunt |
| 3,658,209 A | 4/1972 | Freeman et al. |
| 3,664,548 A | 5/1972 | Broderick |
| 3,666,144 A | 5/1972 | Winder |
| 3,677,441 A | 7/1972 | Nixon, Jr. et al. |
| 3,690,519 A | 9/1972 | Wassilieff |
| 3,722,749 A | 3/1973 | Ishida |
| 3,726,437 A | 4/1973 | Siegel |
| 3,732,509 A | 5/1973 | Florant et al. |
| 3,739,944 A | 6/1973 | Rogerson |
| 3,756,465 A | 9/1973 | Meshberg |
| 3,794,216 A | 2/1974 | Buck |
| 3,817,429 A | 6/1974 | Smrt |
| 3,870,274 A | 3/1975 | Broe |
| 3,885,712 A | 5/1975 | Libit |
| 3,929,259 A | 12/1975 | Fegley et al. |
| 3,952,916 A | 4/1976 | Phillips |
| 3,968,905 A | 7/1976 | Pelton |
| 3,974,941 A | 8/1976 | Mettler |
| 3,980,205 A | 9/1976 | Smart |
| 4,004,550 A | 1/1977 | White et al. |
| 4,006,844 A | 2/1977 | Corris |
| 4,063,664 A | 12/1977 | Meetze, Jr. |
| 4,064,573 A | 12/1977 | Calderone |
| 4,068,575 A | 1/1978 | Difley et al. |
| 4,068,780 A | 1/1978 | Fegley |
| 4,077,542 A | 3/1978 | Petterson |
| 4,096,974 A | 6/1978 | Haber et al. |
| 4,184,612 A | 1/1980 | Freyre |
| 4,235,373 A | 11/1980 | Clark |
| 4,238,055 A | 12/1980 | Staar |
| 4,275,821 A | 6/1981 | Lanno et al. |
| 4,358,860 A | 11/1982 | Church |
| 4,396,152 A | 8/1983 | Abplanalp |
| 4,415,797 A | 11/1983 | Choustoulakis |
| 4,483,466 A | 11/1984 | Gutierrez |
| 4,544,086 A | 10/1985 | Hill et al. |
| 4,658,985 A | 4/1987 | Madsen et al. |
| 4,877,989 A | 10/1989 | Drews et al. |
| 4,967,935 A | 11/1990 | Celest |
| 4,989,755 A | 2/1991 | Shiau |
| 4,993,570 A | 2/1991 | Julian et al. |
| 5,012,961 A | 5/1991 | Madsen et al. |
| 5,014,881 A | 5/1991 | Andris |
| 5,018,963 A | 5/1991 | Diederich |
| 5,025,962 A | 6/1991 | Renfro |
| 5,029,729 A | 7/1991 | Madsen et al. |
| 5,038,972 A | 8/1991 | Muderlak et al. |
| 5,055,822 A | 10/1991 | Campbell et al. |
| 5,098,291 A | 3/1992 | Curtis et al. |
| 5,134,961 A | 8/1992 | Giles et al. |
| 5,137,180 A | 8/1992 | Kieras |
| 5,154,323 A | 10/1992 | Query et al. |
| 5,198,157 A | 3/1993 | Bechet |
| 5,221,025 A | 6/1993 | Privas |
| 5,249,718 A | 10/1993 | Muderlak |
| 5,263,616 A | 11/1993 | Abplanalp |
| 5,297,988 A | 3/1994 | Nishino et al. |
| 5,337,926 A | 8/1994 | Drobish et al. |
| 5,337,929 A | 8/1994 | van der Heijden |
| 5,342,584 A | 8/1994 | Fritz et al. |
| 5,353,744 A | 10/1994 | Custer |
| 5,364,028 A | 11/1994 | Wozniak |
| 5,383,580 A | 1/1995 | Winder |
| RE34,847 E | 2/1995 | Muderlak et al. |
| 5,392,768 A | 2/1995 | Johansson et al. |
| 5,397,028 A | 3/1995 | Jesadanont |
| 5,445,324 A | 8/1995 | Berry et al. |
| 5,447,273 A | 9/1995 | Wozniak |
| 5,447,277 A | 9/1995 | Schluter et al. |
| 5,449,117 A | 9/1995 | Muderlak et al. |
| 5,489,047 A | 2/1996 | Winder |
| 5,503,303 A | 4/1996 | LaWare et al. |
| 5,522,722 A | 6/1996 | Diederich |
| 5,531,344 A | 7/1996 | Winner |
| 5,540,359 A | 7/1996 | Gobbel |
| 5,542,605 A | 8/1996 | Campau |
| 5,549,228 A | 8/1996 | Brown |
| 5,588,565 A | 12/1996 | Miller |
| 5,601,235 A | 2/1997 | Booker et al. |
| 5,622,162 A | 4/1997 | Johansson et al. |
| 5,673,825 A | 10/1997 | Chen |
| 5,676,283 A | 10/1997 | Wang |
| 5,685,456 A | 11/1997 | Goldstein |
| 5,695,091 A | 12/1997 | Winings et al. |
| 5,702,036 A | 12/1997 | Ferrara, Jr. |
| 5,743,251 A | 4/1998 | Howell et al. |
| 5,772,074 A | 6/1998 | Dial et al. |
| 5,787,947 A | 8/1998 | Hertsgaard |
| 5,791,524 A | 8/1998 | Demarest |
| 5,810,265 A | 9/1998 | Cornelius et al. |
| 5,823,390 A | 10/1998 | Muderlak et al. |
| 5,842,602 A | 12/1998 | Pierpoint |
| 5,853,129 A | 12/1998 | Spitz |
| 5,884,808 A | 3/1999 | Muderlak et al. |
| 5,908,140 A | 6/1999 | Muderlak et al. |
| 5,922,247 A | 7/1999 | Shoham et al. |
| 5,924,597 A | 7/1999 | Lynn |
| 5,938,076 A | 8/1999 | Ganzeboom |
| 5,964,403 A | 10/1999 | Miller et al. |
| 6,000,658 A | 12/1999 | McCall, Jr. |
| 6,003,727 A | 12/1999 | Marshall |
| 6,006,957 A | 12/1999 | Kunesh |
| 6,036,108 A | 3/2000 | Chen |
| 6,039,212 A | 3/2000 | Singh |
| 6,089,410 A | 7/2000 | Ponton |
| 6,145,712 A | 11/2000 | Benoist |
| 6,182,904 B1 | 2/2001 | Ulczynski et al. |
| 6,216,925 B1 | 4/2001 | Garon |

(56) References Cited

U.S. PATENT DOCUMENTS

| | | |
|---|---|---|
| 6,220,293 B1 | 4/2001 | Rashidi |
| 6,237,812 B1 | 5/2001 | Fukada |
| 6,249,717 B1 | 6/2001 | Nicholson et al. |
| 6,254,065 B1 | 7/2001 | Ehrensperger et al. |
| 6,260,739 B1 | 7/2001 | Hsiao |
| 6,267,297 B1 | 7/2001 | Contadini et al. |
| 6,276,574 B1 | 8/2001 | Smrt |
| 6,293,442 B1 | 9/2001 | Mollayan |
| 6,293,474 B1 | 9/2001 | Helf et al. |
| 6,321,742 B1 | 11/2001 | Schmidt et al. |
| 6,338,424 B2 | 1/2002 | Nakamura et al. |
| 6,343,714 B1 | 2/2002 | Tichenor |
| 6,394,310 B1 | 5/2002 | Muderlak et al. |
| 6,409,093 B2 | 6/2002 | Ulczynski et al. |
| 6,419,122 B1 | 7/2002 | Chown |
| 6,454,185 B2 | 9/2002 | Fuchs |
| 6,478,199 B1 | 11/2002 | Shanklin et al. |
| 6,510,561 B1 | 1/2003 | Hammond et al. |
| 6,517,009 B2 | 2/2003 | Yahav |
| 6,533,141 B1 | 3/2003 | Petterson et al. |
| 6,540,155 B1 | 4/2003 | Yahav |
| 6,554,203 B2 | 4/2003 | Hess et al. |
| 6,567,613 B2 | 5/2003 | Rymer |
| 6,588,627 B2 | 7/2003 | Petterson et al. |
| 6,612,464 B2 | 9/2003 | Petterson et al. |
| 6,616,363 B1 | 9/2003 | Guillaume et al. |
| 6,619,562 B2 | 9/2003 | Hamaguchi et al. |
| 6,644,507 B2 | 11/2003 | Borut et al. |
| 6,645,307 B2 | 11/2003 | Fox et al. |
| 6,669,105 B2 | 12/2003 | Bryan et al. |
| 6,688,492 B2 | 2/2004 | Jaworski et al. |
| 6,694,536 B1 | 2/2004 | Haygreen |
| 6,701,663 B1 | 3/2004 | Hughel et al. |
| 6,708,849 B1 | 3/2004 | Carter et al. |
| D488,548 S | 4/2004 | Lablaine |
| 6,722,529 B2 | 4/2004 | Ceppaluni et al. |
| 6,739,479 B2 | 5/2004 | Contadini et al. |
| 6,769,580 B2 | 8/2004 | Muderlak et al. |
| 6,776,968 B2 | 8/2004 | Edwards et al. |
| 6,785,911 B1 | 9/2004 | Percher |
| 6,790,408 B2 | 9/2004 | Whitby et al. |
| 6,832,701 B2 | 12/2004 | Schiller |
| 6,837,396 B2 | 1/2005 | Jaworski et al. |
| 6,843,465 B1 | 1/2005 | Scott |
| 6,877,636 B2 | 4/2005 | Speckhart et al. |
| 6,918,512 B2 | 7/2005 | Kondoh |
| 6,926,002 B2 | 8/2005 | Scarrott et al. |
| 6,926,172 B2 | 8/2005 | Jaworski et al. |
| 6,926,211 B2 | 8/2005 | Bryan et al. |
| 6,938,796 B2 | 9/2005 | Blacker et al. |
| 6,971,560 B1 | 12/2005 | Healy et al. |
| 6,974,091 B2 | 12/2005 | McLisky |
| 6,978,947 B2 | 12/2005 | Jin |
| D513,433 S | 1/2006 | Lemaire |
| 6,997,349 B2 | 2/2006 | Blacker et al. |
| 7,000,853 B2 | 2/2006 | Fugere |
| 7,028,917 B2 | 4/2006 | Buthier |
| 7,032,782 B1 | 4/2006 | Ciavarella et al. |
| D520,623 S | 5/2006 | Lablaine |
| 7,044,337 B1 | 5/2006 | Kou |
| 7,051,455 B2 | 5/2006 | Bedford |
| D525,693 S | 7/2006 | Butler et al. |
| D527,472 S | 8/2006 | Barraclough et al. |
| D532,891 S | 11/2006 | Buthier et al. |
| 7,141,125 B2 | 11/2006 | McKechnie et al. |
| D536,059 S | 1/2007 | King et al. |
| D536,082 S | 1/2007 | Pugh |
| 7,168,631 B2 | 1/2007 | Jones |
| 7,182,227 B2 | 2/2007 | Poile et al. |
| D537,914 S | 3/2007 | King et al. |
| D538,915 S | 3/2007 | Anderson et al. |
| 7,192,610 B2 | 3/2007 | Hughes et al. |
| 7,195,139 B2 | 3/2007 | Jaworski et al. |
| D540,931 S | 4/2007 | Luo |
| 7,222,758 B1 | 5/2007 | Scheindel |
| 7,223,361 B2 | 5/2007 | Kvietok et al. |
| 7,249,720 B2 | 7/2007 | Mathiez |
| 7,600,659 B1 | 10/2009 | Greer |
| 7,603,726 B2 * | 10/2009 | Sawalski et al. ............ 4/223 |
| 2002/0020756 A1 | 2/2002 | Yahav |
| 2003/0089734 A1 | 5/2003 | Eberhardt et al. |
| 2003/0132254 A1 * | 7/2003 | Giangreco ............ 222/504 |
| 2004/0011885 A1 | 1/2004 | McLisky |
| 2004/0028551 A1 | 2/2004 | Kvietok et al. |
| 2004/0033171 A1 | 2/2004 | Kvietok et al. |
| 2004/0035949 A1 | 2/2004 | Elkins et al. |
| 2004/0074935 A1 | 4/2004 | Chon |
| 2004/0155056 A1 | 8/2004 | Yahav |
| 2004/0219863 A1 | 11/2004 | Willacy |
| 2005/0004714 A1 | 1/2005 | Chen |
| 2005/0023287 A1 | 2/2005 | Speckhart et al. |
| 2005/0139624 A1 | 6/2005 | Hooks et al. |
| 2005/0155985 A1 | 7/2005 | Meyer |
| 2005/0201944 A1 | 9/2005 | Kvietok et al. |
| 2005/0224596 A1 | 10/2005 | Panopoulos |
| 2005/0252930 A1 | 11/2005 | Contadini et al. |
| 2005/0279853 A1 | 12/2005 | McLeisch et al. |
| 2006/0011737 A1 | 1/2006 | Amenos et al. |
| 2006/0037532 A1 | 2/2006 | Eidson |
| 2006/0060615 A1 | 3/2006 | McLisky |
| 2006/0076366 A1 | 4/2006 | Furner et al. |
| 2006/0081661 A1 | 4/2006 | Lasserre et al. |
| 2006/0083632 A1 | 4/2006 | Hammond et al. |
| 2006/0118658 A1 | 6/2006 | Corkhill et al. |
| 2006/0124477 A1 | 6/2006 | Cornelius et al. |
| 2006/0140901 A1 | 6/2006 | McKechnie |
| 2006/0151546 A1 | 7/2006 | McLisky |
| 2006/0153733 A1 | 7/2006 | Sassoon |
| 2006/0175341 A1 | 8/2006 | Rodrian |
| 2006/0175357 A1 | 8/2006 | Hammond |
| 2006/0175426 A1 | 8/2006 | Schramm et al. |
| 2006/0191955 A1 | 8/2006 | McLisky |
| 2006/0196576 A1 | 9/2006 | Fleming et al. |
| 2006/0210421 A1 | 9/2006 | Hammond et al. |
| 2006/0219740 A1 | 10/2006 | Bayer |
| 2006/0229232 A1 | 10/2006 | Contadini et al. |
| 2006/0243762 A1 | 11/2006 | Sassoon |
| 2007/0012718 A1 | 1/2007 | Schramm et al. |
| 2007/0062980 A1 | 3/2007 | Bates et al. |
| 2007/0071933 A1 | 3/2007 | Gavelli et al. |
| 2007/0087953 A1 | 4/2007 | McKechnie et al. |
| 2007/0093558 A1 | 4/2007 | Harper et al. |
| 2007/0138326 A1 | 6/2007 | Hu |
| 2007/0158359 A1 | 7/2007 | Rodrian |
| 2009/0045219 A1 * | 2/2009 | Helf et al. ............ 222/52 |
| 2009/0045220 A1 * | 2/2009 | Helf et al. ............ 222/52 |

FOREIGN PATENT DOCUMENTS

| | | |
|---|---|---|
| EP | 0826607 | 3/1998 |
| EP | 0826608 | 3/1998 |
| EP | 1184083 | 3/2002 |
| EP | 1214949 | 6/2002 |
| EP | 1316514 | 6/2003 |
| EP | 1382399 | 1/2004 |
| EP | 1430958 | 6/2004 |
| EP | 1522506 | 4/2005 |
| EP | 1328757 | 5/2006 |
| EP | 1695720 | 8/2006 |
| EP | 1702512 | 9/2006 |
| EP | 1702513 | 9/2006 |
| EP | 1709980 | 10/2006 |
| EP | 1726315 | 11/2006 |
| FR | 1497250 | 10/1967 |
| GB | 1033025 | 6/1966 |
| JP | 56037070 | 4/1981 |
| JP | 56044060 | 4/1981 |
| JP | 56044061 | 4/1981 |
| JP | 56044062 | 4/1981 |
| JP | 56070865 | 6/1981 |
| JP | 57174173 | 10/1982 |
| JP | 01-223904 | 9/1989 |
| JP | 03-085169 | 4/1991 |
| JP | 03-085170 | 4/1991 |

(56) References Cited

FOREIGN PATENT DOCUMENTS

| | | |
|---|---|---|
| JP | 08-336580 | 12/1996 |
| JP | 10216577 | 8/1998 |
| JP | 11-076879 | 3/1999 |
| JP | 11-236083 | 8/1999 |
| JP | 2001048254 | 2/2001 |
| JP | 2002068344 | 3/2002 |
| JP | 2002113398 | 4/2002 |
| JP | 2002-238658 | 8/2002 |
| JP | 2003246380 | 9/2003 |
| JP | 2003311191 | 11/2003 |
| JP | 2005081223 | 3/2005 |
| WO | 9115409 | 10/1991 |
| WO | 9519304 | 7/1995 |
| WO | 9529106 | 11/1995 |
| WO | 9934266 | 7/1999 |
| WO | 0047335 | 8/2000 |
| WO | 0064802 | 11/2000 |
| WO | 0075046 | 12/2000 |
| WO | 0078467 | 12/2000 |
| WO | 0126448 | 4/2001 |
| WO | 0240177 | 5/2002 |
| WO | 0240376 | 5/2002 |
| WO | 02072161 | 9/2002 |
| WO | 02079679 | 10/2002 |
| WO | 02087976 | 11/2002 |
| WO | 02094014 | 11/2002 |
| WO | 03037748 | 5/2003 |
| WO | 03037750 | 5/2003 |
| WO | 03042068 | 5/2003 |
| WO | 03062094 | 7/2003 |
| WO | 03062095 | 7/2003 |
| WO | 03068412 | 8/2003 |
| WO | 03068413 | 8/2003 |
| WO | 03082709 | 10/2003 |
| WO | 03086902 | 10/2003 |
| WO | 03086947 | 10/2003 |
| WO | 03099682 | 12/2003 |
| WO | 03104109 | 12/2003 |
| WO | 2004043502 | 5/2004 |
| WO | 2004067963 | 8/2004 |
| WO | 2004073875 | 9/2004 |
| WO | 2004093927 | 11/2004 |
| WO | 2004093928 | 11/2004 |
| WO | 2005011560 | 2/2005 |
| WO | 2005014060 | 2/2005 |
| WO | 2005018691 | 3/2005 |
| WO | 2005023679 | 3/2005 |
| WO | 2005027630 | 3/2005 |
| WO | 2005048718 | 6/2005 |
| WO | 2005070474 | 8/2005 |
| WO | 2005072059 | 8/2005 |
| WO | 2005072522 | 8/2005 |
| WO | 2005079583 | 9/2005 |
| WO | 2005084721 | 9/2005 |
| WO | 2006005962 | 1/2006 |
| WO | 2006012248 | 2/2006 |
| WO | 2006013321 | 2/2006 |
| WO | 2006013322 | 2/2006 |
| WO | 2006044416 | 4/2006 |
| WO | 2006051267 | 5/2006 |
| WO | 2006054103 | 5/2006 |
| WO | 2006056762 | 6/2006 |
| WO | 2006058433 | 6/2006 |
| WO | 2006064187 | 6/2006 |
| WO | 2006074454 | 7/2006 |
| WO | 2006087514 | 8/2006 |
| WO | 2006087515 | 8/2006 |
| WO | 2006095131 | 9/2006 |
| WO | 2006104993 | 10/2006 |
| WO | 2006105652 | 10/2006 |
| WO | 2006108043 | 10/2006 |
| WO | 2006134353 | 12/2006 |
| WO | 2007028954 | 3/2007 |
| WO | 2007029044 | 3/2007 |
| WO | 2007036724 | 4/2007 |
| WO | 2007045826 | 4/2007 |
| WO | 2007045827 | 4/2007 |
| WO | 2007045828 | 4/2007 |
| WO | 2007045831 | 4/2007 |
| WO | 2007045832 | 4/2007 |
| WO | 2007045834 | 4/2007 |
| WO | 2007045835 | 4/2007 |
| WO | 2007045859 | 4/2007 |
| WO | 2007052016 | 5/2007 |
| WO | 2007064188 | 6/2007 |
| WO | 2007064189 | 6/2007 |
| WO | 2007064197 | 6/2007 |
| WO | 2007064199 | 6/2007 |
| WO | 2009/025741 A | 2/2009 |
| WO | 2009023208 A | 2/2009 |

OTHER PUBLICATIONS

International Search Report and Written Opinion dated Nov. 13, 2008 Appl. No. PCT/US2008/009661.

International Search Report and Written Opinion dated Dec. 23, 2008 Appl. No. PCT/US2008/009663.

* cited by examiner

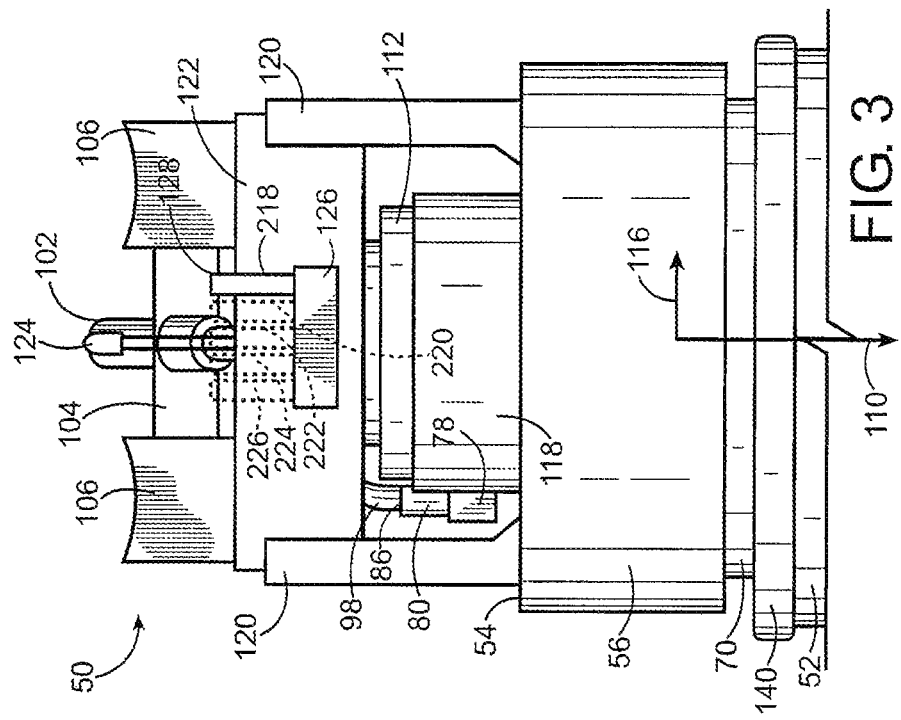
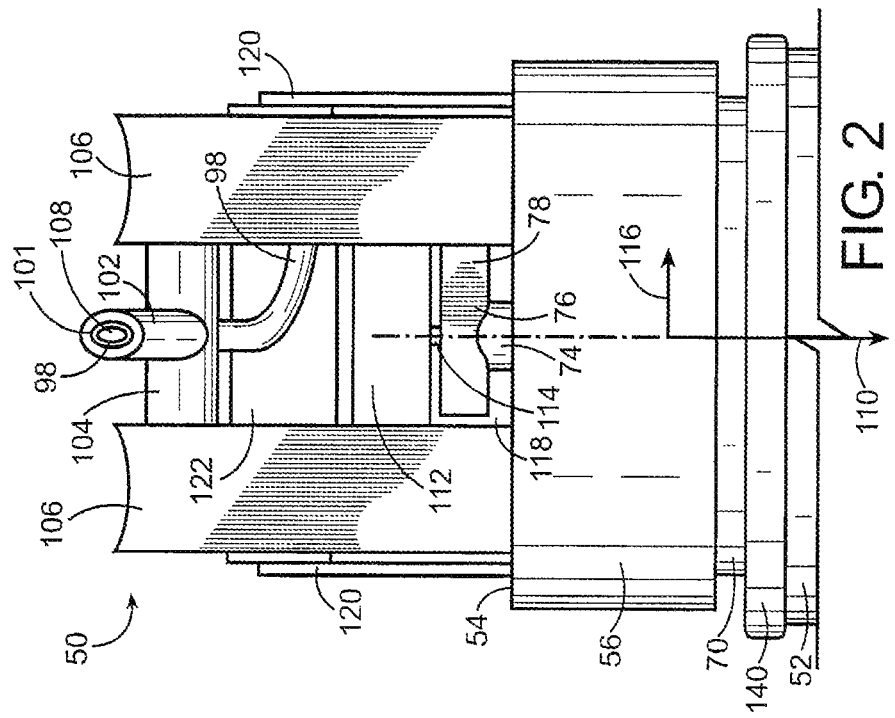

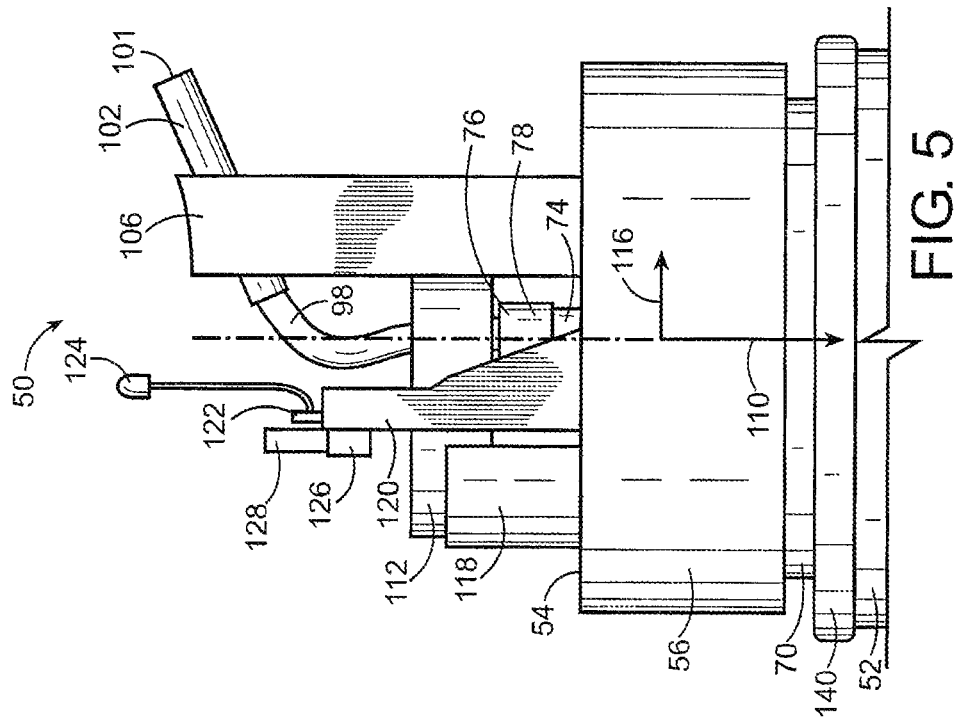
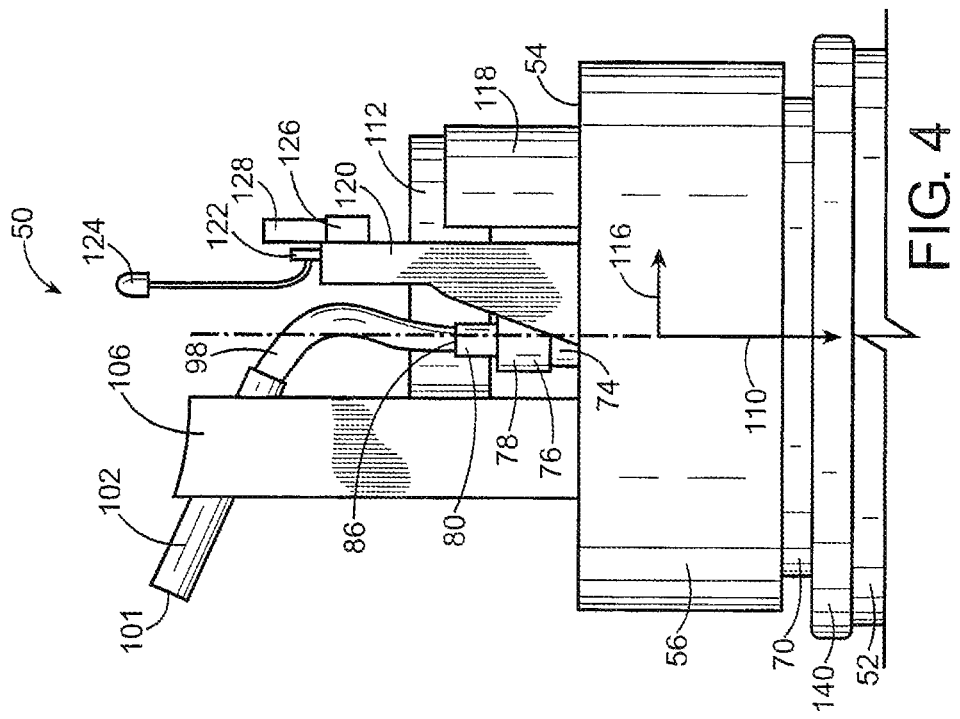

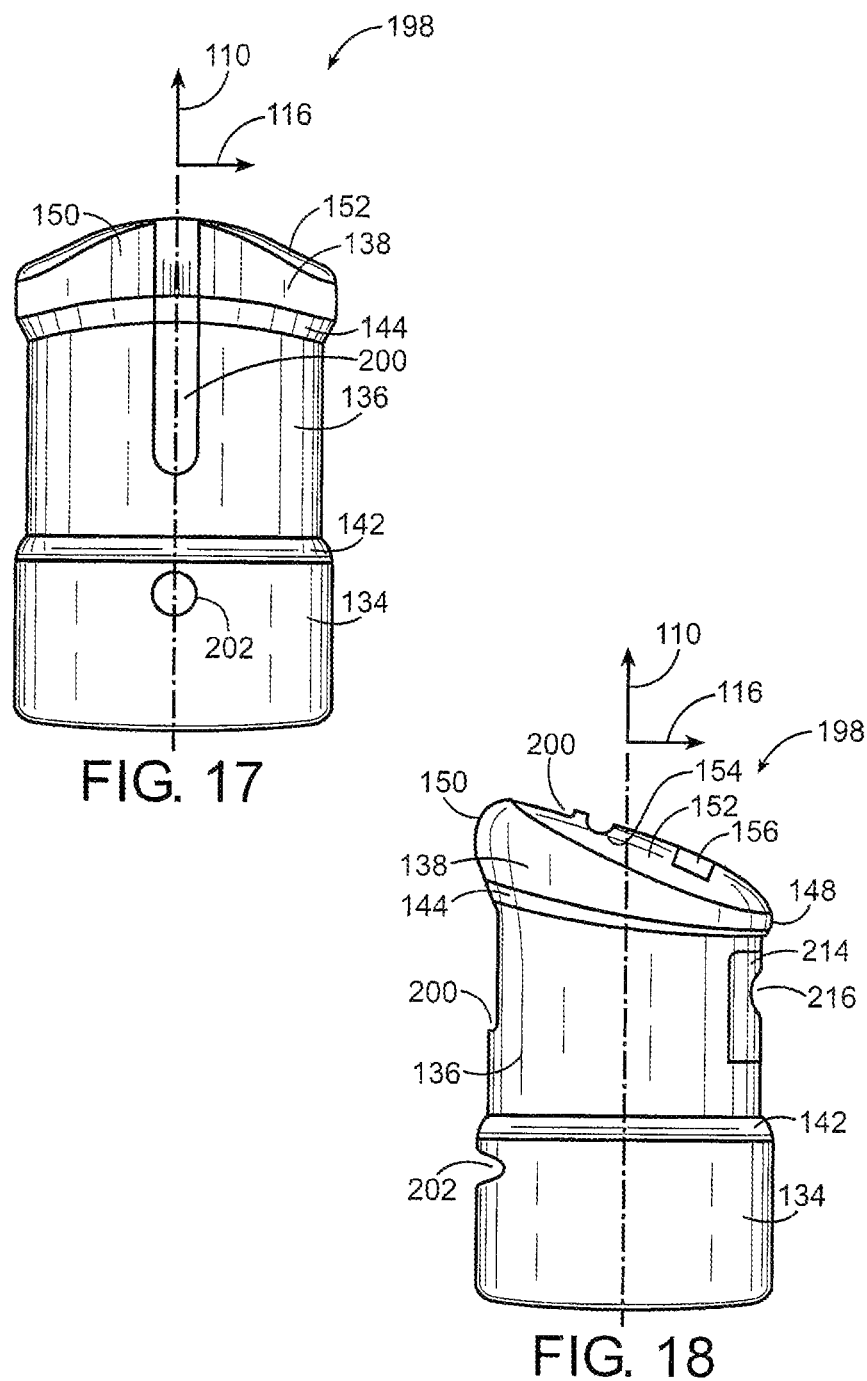

VOLATILE MATERIAL DISPENSER

CROSS REFERENCE TO RELATED APPLICATIONS

This application is a divisional of U.S. patent application Ser. No. 12/054,054, filed Mar. 24, 2008.

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Invention

The present disclosure relates generally to a valve activation system for the release of a volatile material from a container, and more particularly to a valve activation system having a flexible tube adapted to dispense an aerosolized fluid from a container having a tilt-activated valve stem.

2. Description of the Background of the Invention

Aerosol containers are commonly used to store and dispense volatile materials such as air fresheners, deodorants, insecticides, germicides, decongestants, perfumes, and the like. The volatile material is stored under compression and typically in a liquid state within a container. A release valve on the container controls release of the volatile material contained under compression therein. The release valve typically has a valve stem that extends outwardly from the valve, wherein the valve is activated by the valve stem and the volatile material flows out of the container through the valve stem. In such a release valve, the valve is activated by a displacement of the valve stem with respect to a valve body. The valve stem may be displaced along a longitudinal axis of the valve stem, i.e., axially, or the valve stem may be tilted or displaced in a direction transverse to the longitudinal axis of the valve stem, i.e., radially.

Activation of a release valve may be accomplished by an automated system or manually. In manual activation, a user may adjust an activation force applied to the valve as required to achieve a desired release. Therefore, consideration of applied force requirements is generally less important to design of manually activated release valves. Conventional actuator mechanisms may include motor driven linkages that apply downward pressure to depress the nozzle and open the valve within the container. Typically, these actuator mechanisms are unwieldy and are not readily adaptable to be used in a stand-alone manner and a hand-held manner. Further, many of these actuator mechanisms exhibit a great deal of power consumption. Generally, valves having tilt-activated valve stems require less force for activation than valves having vertically activated valve stems. Release valves requiring smaller activation forces are advantageous because such valves require less power to activate. Decreased power consumption will allow for longer power source life times. Smaller activation forces are also advantageous for automated activation because smaller required forces allow for simpler, smaller, and/or less costly automated designs.

Existing automated valve activation systems for valves having tilt-activated valve stems are complex and may be difficult and expensive to manufacture. Complex systems including gears, springs, and precise interactions of a multitude of moving parts may also require more power to operate, have a greater tendency to break, and may be too large to fit within an overcap for placement on a volatile material container.

Another disadvantage of current valve activation systems for valves having tilt-activated valve stems is the limited ability to control the direction in which the volatile material is released. In an axially activated valve, the volatile material is released along the longitudinal axis of the valve stem no matter how far the valve stem is depressed axially. However, in a tilt-activated valve stem, the direction of release depends on how far the tilt-activated valve stem has been displaced radially and/or the circumferential direction of the radial displacement. This limited ability to control the direction of release limits the type of overcap that may be used with a tilt-activated valve stem. To prevent a portion of the released volatile material from being captured within an overcap, the overcap must include an aperture large enough to accommodate a full range of release directions.

SUMMARY OF THE INVENTION

According to one aspect of the invention, a volatile material dispenser includes a drive unit adapted to be mounted on a container. The drive unit is adapted to be activated in response to a signal from at least a sensor to radially displace a tilt-activated valve stem of the container. The volatile material dispenser further includes a flexible tube having a discharge end fixedly held with respect to the container. The flexible tube is adapted to be in fluid communication with the tilt-activated valve stem.

BRIEF DESCRIPTION OF THE DRAWINGS

FIG. 2 is a front elevational view of the volatile material dispenser of FIG. 1;

FIG. 3 is a rear elevational view of the volatile material dispenser of FIG. 1;

FIG. 4 is a right side elevational view of the volatile material dispenser of FIG. 1;

FIG. 5 is a left side elevational view of the volatile material dispenser of FIG. 1;

FIG. 17 is a front elevational view of a housing for the volatile material dispenser of FIG. 16 including a slot and an aperture to accommodate a sensor;

FIG. 18 is a right side elevational view of the housing of FIG. 17 further depicting a depressible panel.

Other aspects and advantages of the present invention will become apparent upon consideration of the following detailed description, wherein similar structures have similar reference numerals.

DETAILED DESCRIPTION

FIGS. 1-7 depict a volatile material dispenser 50 adapted to be mounted on a container 52 (see FIGS. 1-5 and 7). The volatile material dispenser 50 discharges fluid from the container 52 upon the occurrence of a particular condition. The condition could be the manual activation of the volatile material dispenser 50 or the automatic activation of the volatile material dispenser 50 in response to an electrical signal from a timer or a sensor. The fluid discharged may be a fragrance or insecticide disposed within a carrier liquid, a deodorizing liquid, or the like. The fluid may also comprise other actives, such as sanitizers, air fresheners, odor eliminators, mold or mildew inhibitors, insect repellents, and/or the like, and/or that have aromatherapeutic properties. The fluid alternatively comprises any fluid known to those skilled in the art that may be dispensed from the container 52. The volatile material dispenser 50 is therefore adapted to dispense any number of different fluid formulations.

Figure 1:
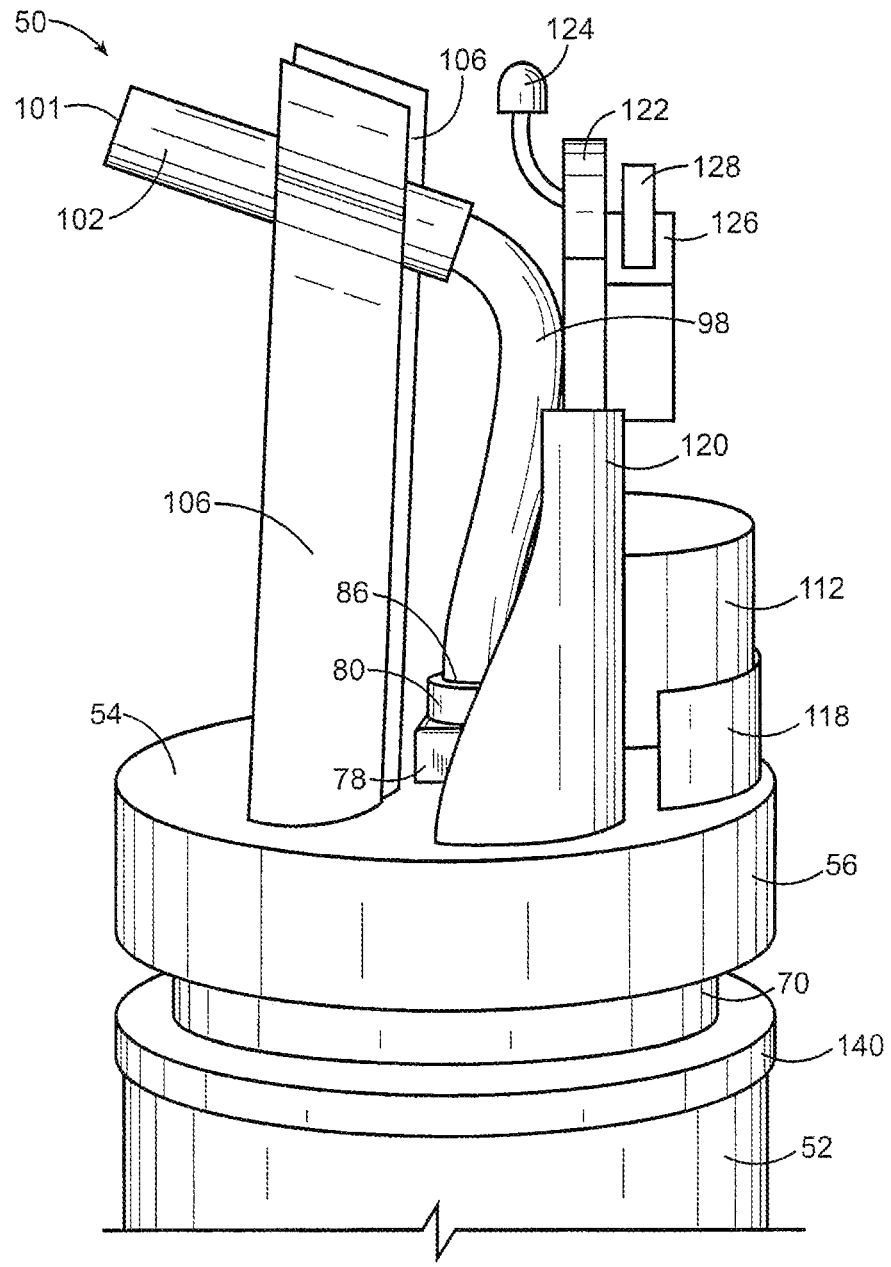
FIG. 1 is an isometric view of one embodiment of a volatile material dispenser mounted on a fluid container.
Figure 6:
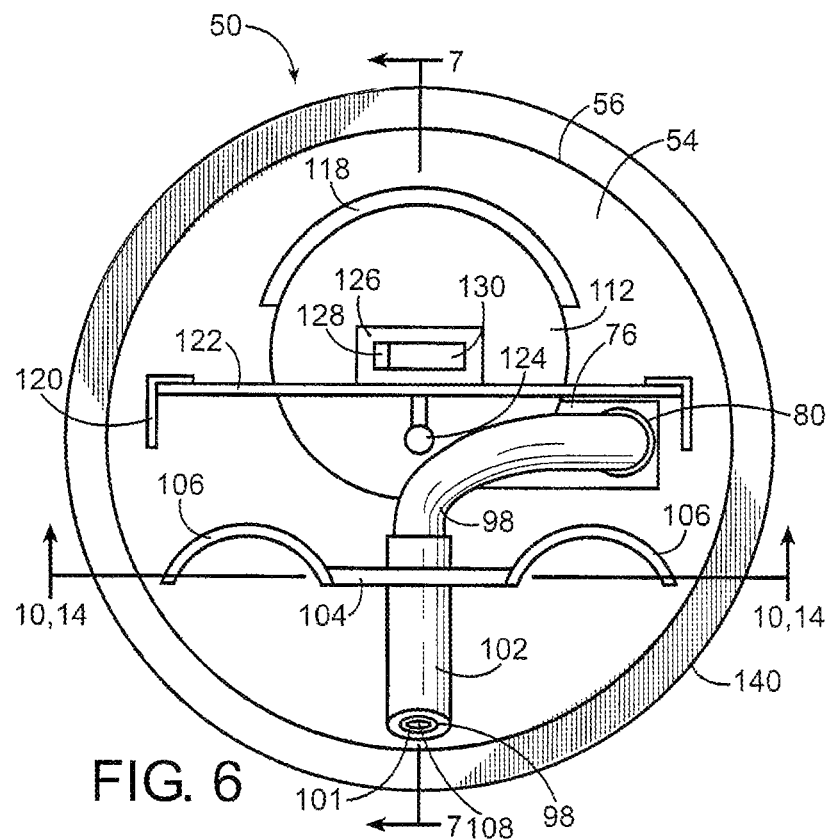
FIG. 6 is a top plan view of the volatile material dispenser of FIG. 1.
Figure 7:
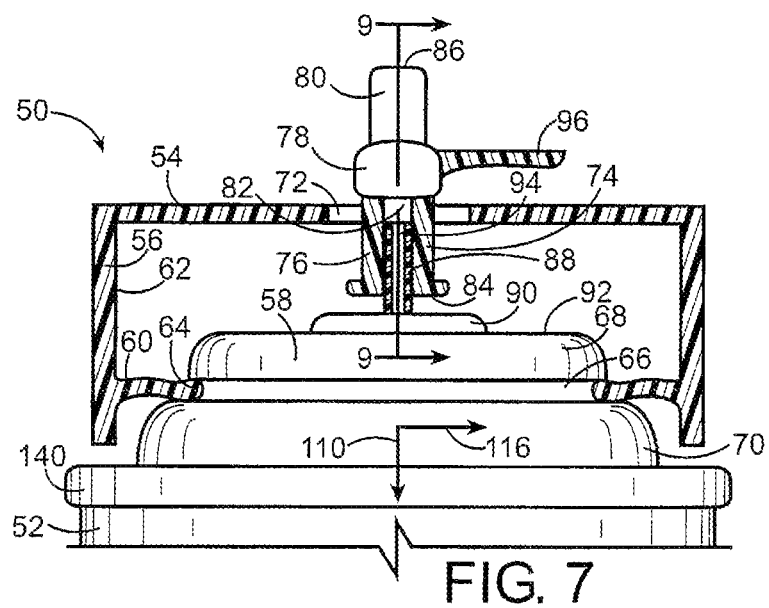
FIG. 7 is an right side elevational view partly in section taken along the lines 7-7 of FIG. 6 with structure above a platform of the volatile material dispenser omitted for purposes of clarity.

The volatile material dispenser 50 includes a platform 54 that is disposed on a cylindrical section 56. As shown in FIG. 7, the cylindrical section 56 is shaped to snap fit onto an upper end 58 of the container 52. FIG. 7 shows that the present embodiment includes an annular protrusion 60 projecting inwardly from an inner circumference 62 of the cylindrical section 56. A distal end 64 of the annular protrusion 60 forms a snap fit with an undercut 66 of the container 52 disposed between an upper mounting cup 68 and a lower mounting cup 70 on the upper end 58 of the container 52. The container 52 may be an aerosol container of any size and volume known to those skilled in the art.

Figure 8:
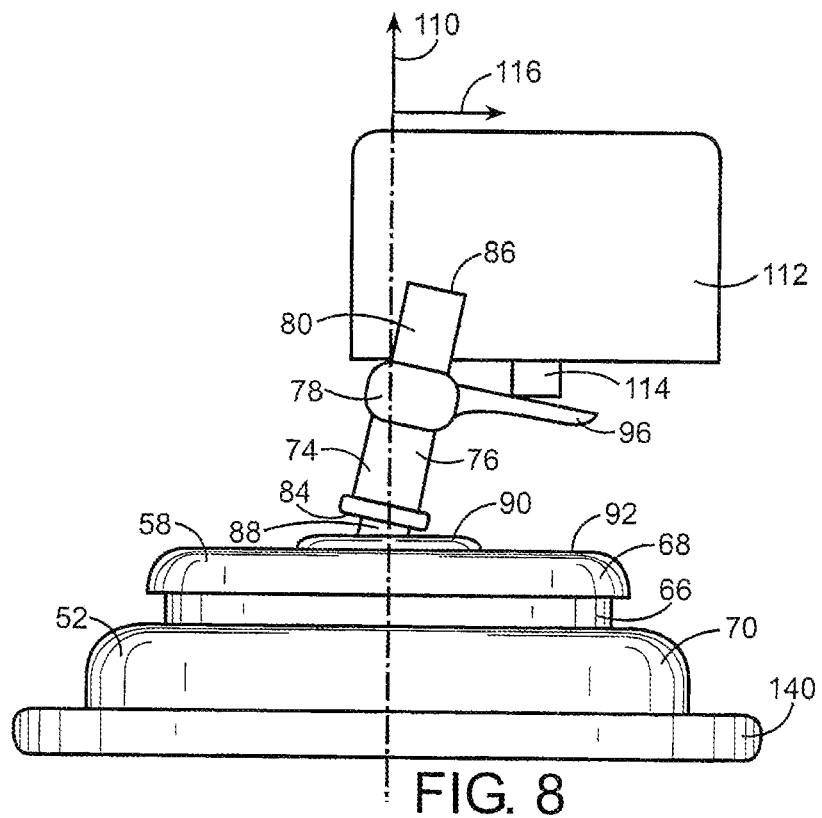
FIG. 8 is right side elevational view of the volatile material dispenser of FIG. 1 with mounting brackets and support components omitted for purposes of clarity.
Figure 9:
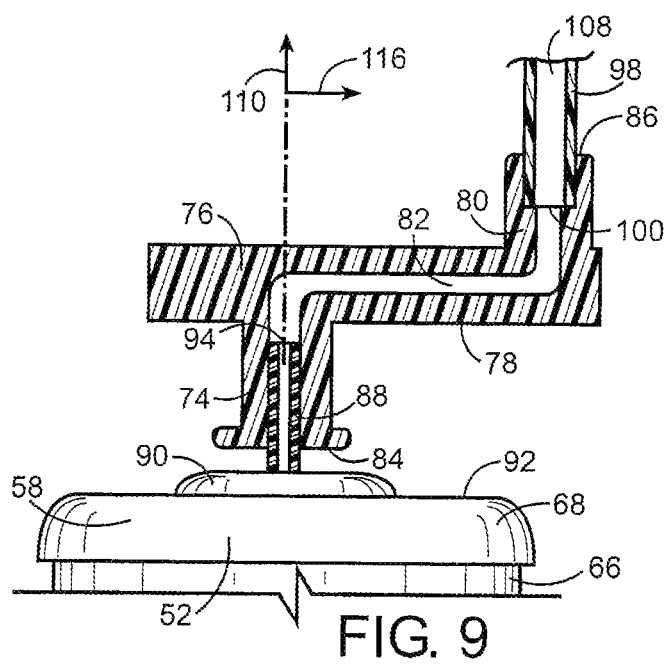
FIG. 9 is a partial cross-sectional view of the volatile material dispenser taken generally along lines 9-9 of FIG. 7, wherein only the fluid container, a discharge conduit, and a flexible tube are shown for purposes of clarity.

Referring to FIG. 7, an aperture 72 is provided in the platform 54. The aperture 72 accommodates an inlet portion 74 of a discharge conduit 76, as shown in FIGS. 7-9. As best seen in FIG. 9, the discharge conduit 76 includes a transverse medial portion 78 that connects the inlet portion 74 to an outlet portion 80. A continuous aperture 82 is disposed through the discharge conduit 76 from a base end 84 to an outlet end 86. A valve assembly (not shown) within the container 52 includes a tilt-activated valve stem 88 extending upwardly through a collar 90 disposed on an end surface 92 of the container 52. The base end 84 of the discharge conduit 76 is attached, e.g., by a press fit, over the tilt-activated valve stem 88. The continuous aperture 82 is in fluid communication with a bore 94 disposed through the tilt-activated valve stem 88. As seen in FIGS. 7 and 8, the discharge conduit 76 further includes a flange 96 that extends radially from the inlet portion 74 thereof. The tilt-activated valve stem 88 may be of the type described in Van der Heijden U.S. Pat. No. 4,064,782.

Figure 10:
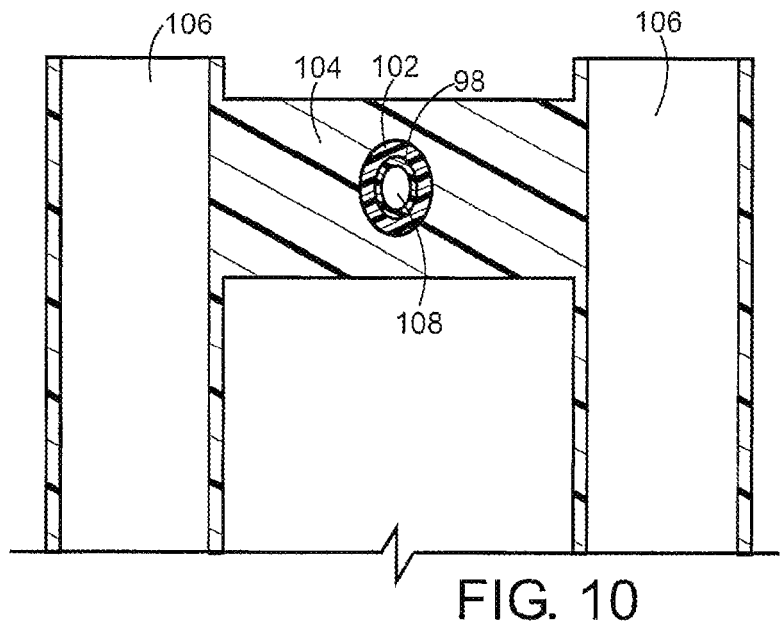
FIG. 10 is a cross-sectional view of a guide member of the volatile material dispenser of FIG. 1 taken generally along the lines 10-10 of FIG. 6, wherein structure behind the plane of section has been omitted for purposes of clarity.

A flexible tube 98 includes an inlet end 100 that is attached to the outlet end 86 of the discharge conduit 76 as shown in FIGS. 1, 3, 4, and 9. The flexible tube 98 also includes a discharge end 101 as shown in FIGS. 1, 2, 4-6, 15, and 16. In the present embodiment, a sleeve 102 is attached over the flexible tube 98 adjacent the discharge end 101 thereof as shown in FIGS. 2, 6, 10, 14, and 15, e.g., by a press fit, an adhesive, a fastener, or by any other means of attachment. A guide member 104, such as shown in FIGS. 2, 3, 6, and 10, fixedly holds the sleeve 102 to immobilize the discharge end 101 of the flexible tube 98 with respect to the container 52. The guide member 104 may be attached proximate to the discharge end 101 of the flexible tube 98 as shown in FIG. 10, e.g., by a press fit therearound, by an adhesive, by a fastener, or by any means of attachment known to one having skill in the art. Further, it is contemplated in other embodiments that the guide member 104 may directly hold the flexible tube 98 by removing the sleeve 102. In this embodiment, the guide member 104 is attached between a pair of vertically extending battery holders 106 as shown in FIGS. 1-3, 6, and 10.

Figure 14:
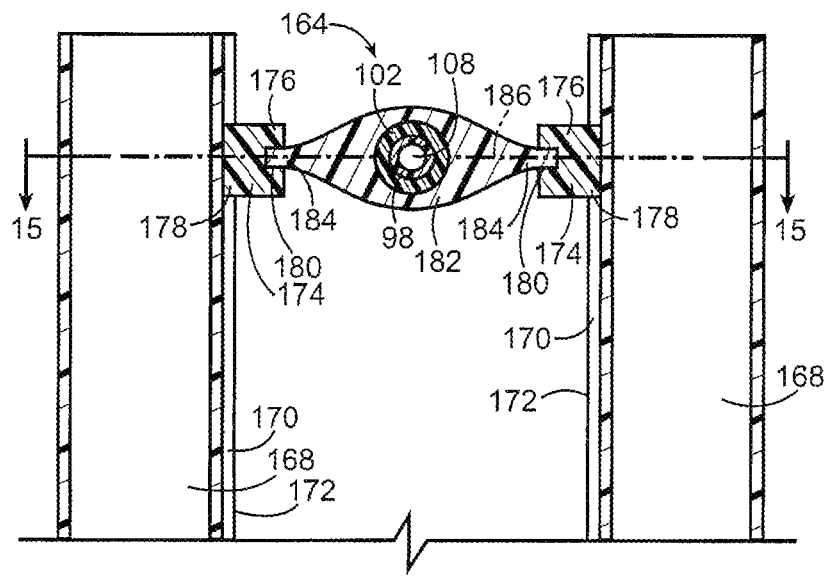
FIG. 14 is a cross-sectional view of a different embodiment showing an adjustable guide member taken along the lines 14-14 of FIG. 6, wherein structure behind the plane of section has been omitted for purposes of clarity.

The flexible tube 98 has a continuous bore 108 therethrough as shown in FIGS. 2, 6, 9, 10, 14, and 15 that provides fluid communication between the inlet end 100 and the discharge end 101 thereof. The tube may have an outer surface that is smooth or crenellated and that has a cross section that is circular, e.g., as depicted in FIG. 14, or that is pentagonal, hexagonal, elliptical, triangular, square, octagonal, or any other shape known to one having ordinary skill in the art. Likewise, the bore 108 through the tube 98 may have an inner surface that is smooth or crenellated and may have any desired cross section, e.g., circular, elliptical, square, triangular, pentagonal, hexagonal, octagonal, or any other shape that is the same or different than the cross section of the outer surface, as known to one having ordinary skill in the art. Further, the cross sections of the outer surface of the tube 98 and the inner surface of the bore 108 may each be uniform or variable between the inlet end 100 and the discharge end 101 of the tube 98.

In a non-active state, the tilt-activated valve stem 88 is coincident with a longitudinal axis 110 of the container 52 as shown in FIG. 7. A drive unit, e.g., a solenoid assembly 112 driving a plunger 114, as shown in FIG. 8, engages the flange 96 on the discharge conduit 76 when activated. A representative solenoid assembly, for example, is a Ledex® Low Profile Battery Operated Linear Solenoid, size number 1ECM, model number 282342-025, which is available from Johnson Electric, Industry Products Group, Vandalia, Ohio. The 1ECM-282342-025 solenoid weighs 42.5 grams, is 25.4 mm in diameter and 13.5 mm tall. When operating on a 50% maximum duty cycle, the 1ECM-282342-025 solenoid nominally requires 2.9 volts DC, generates 2.2 Newtons (0.49 pounds) of force through a nominal stroke of 2 mm, and can remain energized for a maximum of 162 seconds.

As shown in FIG. 8, downward extension of the plunger 114 in a direction parallel with the longitudinal axis 110 causes downward displacement of the flange 96. The discharge conduit 76 is sufficiently rigid such that downward displacement of the flange 96 causes the base end 84 of the discharge conduit 76 to be displaced in a radial direction 116 away from the longitudinal axis 110, whereupon the tilt-activated valve stem 88 disposed within the base end 84 is also displaced in a radial direction 116 away from the longitudinal axis 110. When a distal end of the tilt-activated valve stem 88 is displaced radially to a sufficient degree, i.e., into an operable position, the valve assembly within the container 52 is opened and the contents of the container 52 are discharged through the bore 94 of the tilt-activated valve stem 88. In the terminology of the axisymmetric coordinate system used herein, a radial displacement includes any displacement of the distal end of the tilt-activated valve stem 88 away from the longitudinal axis 110. Such a radial displacement may therefore be characterized as a lateral or a transverse displacement of the distal end of the tilt-activated valve stem 88. Release of fluid via the volatile material dispenser 50 through the tilt-activated valve stem 88 may be problematic in prior art devices due to the lack of control of a specific direction of release, as mentioned hereinabove. However, the inclusion of the flexible tube 98 attached to the discharge conduit 76 allows the fluid to be specifically directed in the present embodiment because the discharge end 101 of the flexible tube 98 is fixedly held with respect to the container 52 by the guide member 104.

The contents of the container 52 may be discharged in a continuous or metered dose. Further, the discharging of the contents of the container 52 may be effected in any number of ways, e.g., a discharge may comprise a partial metered dose or multiple consecutive discharges. It is also contemplated that any appropriate drive assembly having a capacity to downwardly displace the flange 96 as is known to one skilled in the art may be used to radially displace the tilt-activated valve stem 88. For example, it is contemplated that the drive assemblies shown in application Ser. Nos. 11/801,554 and 11/893,456 may be adapted to work with the presently described embodiments.

Referring now to FIGS. 1-6, the solenoid assembly 112 is attached to the platform 54 by an attachment wall 118. In other embodiments, the solenoid assembly 112 may be attached to the platform 54 by support screws (not shown) extending from the solenoid assembly 112 or by other attachment mechanisms known to one having skill in the art. A pair of support pillars 120 extends upwardly from the platform 54. A printed circuit board 122 is held between the support pillars 120 and above the solenoid assembly 112. The printed circuit board 122 includes a light emitting diode (LED) 124 affixed to a front side thereof and extending upwardly therefrom. A linear switch assembly 126 is attached to a rear side of the printed circuit board 122. A positioning finger 128 extends from a rectangular slot 130 in the linear switch assembly 126.

Figure 11:
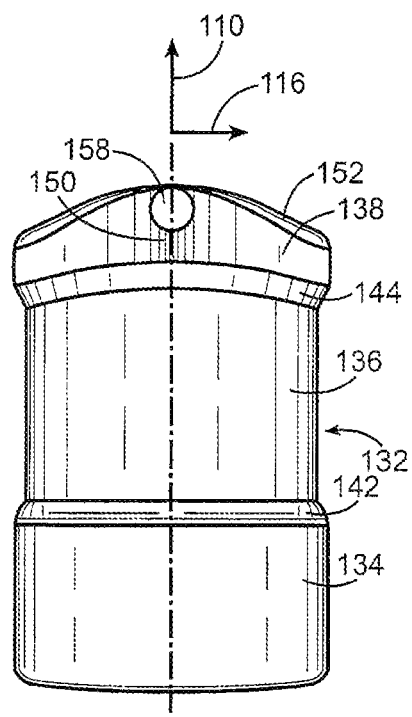
FIG. 11 is a front elevational view of a housing for the volatile material dispenser of FIG. 1.
Figure 12:
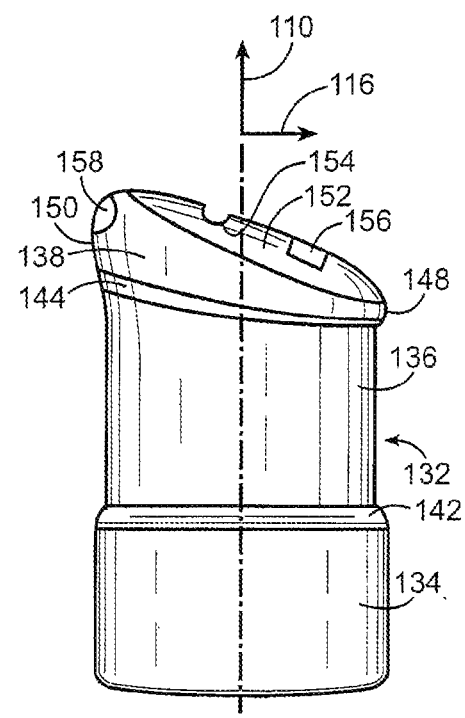
FIG. 12 is a right side elevational view of the housing of FIG. 11.
Figure 13:
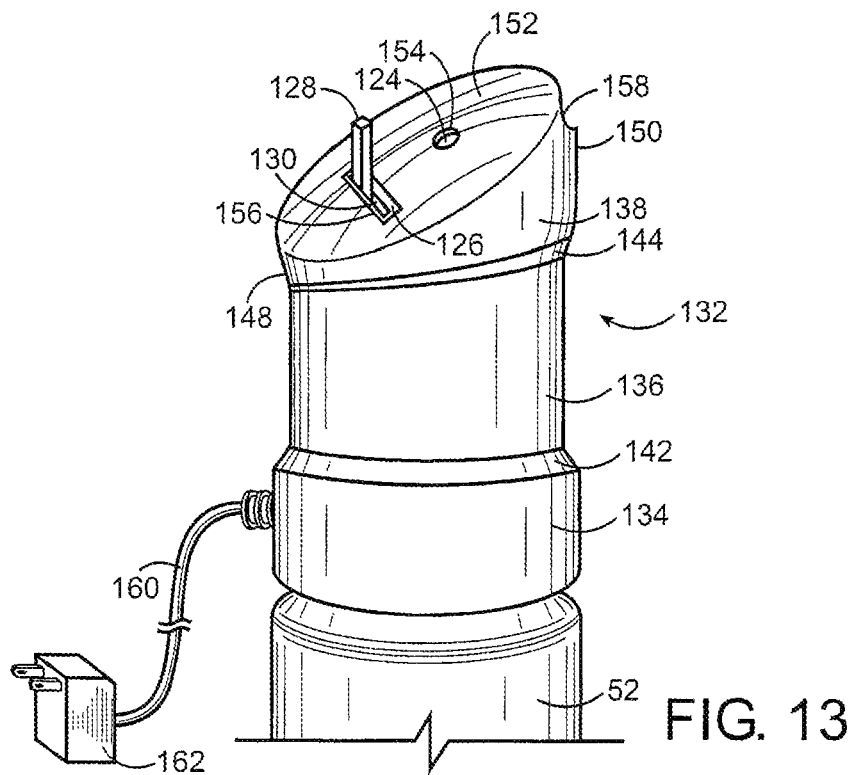
FIG. 13 is a left and rear side isometric view of another embodiment of a housing for the volatile material dispenser of FIG. 1 similar to the ones shown in FIGS. 12 and 13, except the present embodiment includes an AC connector and is mounted on a container.

As shown in FIGS. 11-13, a housing 132 has a generally cylindrical shape and includes a lower portion 134, a medial portion 136 and an upper portion 138. The lower portion 134 includes an inwardly projecting annular lip (not shown) at a bottom end thereof. The annular lip is adapted to snap fit over a ridge 140 (see FIGS. 1-8) extending outwardly from an outer circumference of the container 52 to allow the housing 132 to be mounted on the container 52, such as shown in FIG. 13. The medial portion 136 of the housing 132 has a slightly smaller diameter than the lower portion 134 and is connected thereto by a lower tapering shoulder 142. An upper tapering shoulder 144 connects the medial portion 136 to the upper portion 138, which has a diameter approximately equal to that of the lower portion 134.

The housing 132 includes a back side 148 and a front side 150. The upper portion 138 includes a convex top surface 152 that generally slopes upwardly from the back side 148 to the front side 150. A circular aperture 154 is disposed through the top surface 152 to accommodate the LED 124 and a rectangular aperture 156 is disposed through the top surface 152 to accommodate the linear switch assembly 126. The front side 150 of the upper portion 138 includes an aperture 158 disposed therethrough for accommodation of the discharge end 101 of the flexible tube 98.

As discussed hereinabove, use of the tilt-activated valve stem 88 in prior art devices is problematic due to an inherent lack of control of a specific direction of release of the fluid. As a result, fluid released through the tilt-activated valve stem 88 may tend to inappropriately spray into the housing 132, thereby undesirably coating the inner surfaces of the housing 132 instead of being directed to the environment. Inclusion of the flexible tube 98 prevents fluid released through the tilt-activated valve stem 88 from spraying into the inside of the housing 132. The flexible tube 98 allows the aperture 158 to be positioned on the housing 132 in a desired location to allow convenient and accurate directional spraying of the fluid from the volatile material dispenser 50. Further, the flexible tube 98 allows the aperture 158 to have a size or a shape without regard to directional spraying limitations of the tilt-activated valve stem 88.

The housing 132 may be retained on the container 52 in any manner known by those skilled in the art. For example, the retention structures described in Balfanz U.S. Pat. No. 4,133,408, Demarest U.S. Pat. No. 5,027,982, and Demarest et al. U.S. Pat. No. 5,609,605 may be used in connection with any of the embodiments described herein. The housing 132 may also be integral with and/or connectable to the volatile material dispenser 50, for example via a connection at the cylindrical section 56 thereof. Illustratively, the housing 132 may include an annular lip (not shown) projecting inwardly from an inner circumferential surface thereof. The annular lip may be adapted to snap over a bottom edge of the cylindrical section 56 or a corresponding outwardly protruding lip (not shown) on an outer circumferential surface of the cylindrical section 56. The housing may thus be retained directly on the volatile material dispenser 50 in addition to, or instead of, being retained on the container 52. Further, any of the aesthetic aspects of the housing 132 described herein may be modified in any manner known by one skilled in the art, e.g., the medial portion 136 and the lower and upper tapering shoulders 142, 144 could be eliminated or the housing 132 could be provided with a different shape.

Each of the vertically extending battery holders 106 is adapted to retain a battery, e.g., a size AA or AAA battery, therein to provide a D.C. power source to the drive unit. In some embodiments, the batteries may be interchangeable with other power sources. For example, the batteries may be replaced by a rechargeable Nickel-Cadmium battery or battery pack (not shown) having an electrical lead 160 that may be used to connect the battery pack to an A.C. power adapter 162 having an appropriate power transformer and A.C./D.C. converter as known to those of skill in the art (see FIG. 13).

Figure 15:
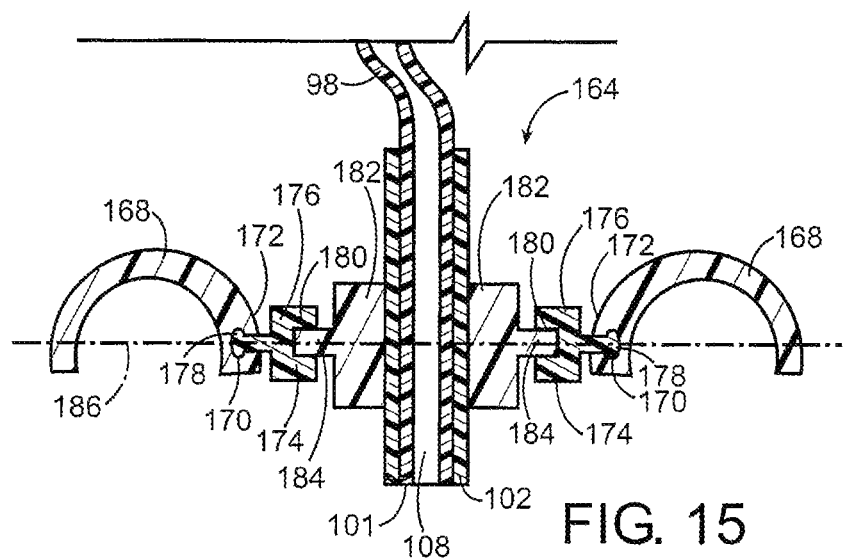
FIG. 15 is a partial cross-sectional view of the adjustable guide member of FIG. 14 taken generally along the lines 15-15 of FIG. 14.

In another embodiment, the discharge end 101 of the flexible tube 98 is fixedly held with respect to the container 52 by an adjustable guide member 164, e.g., such as the one shown in FIGS. 14 and 15. In this embodiment, a volatile material dispenser 166 (see FIG. 16) includes a pair of vertically extending battery holders 168, each including a groove 170 running vertically along inwardly facing edges 172 thereof. The adjustable guide member 164 includes a pair of end brackets 174. Each end bracket 174 has a support body 176 and a tongue 178 extending from the support body 176 and sized to snugly fit within one of the grooves 170. Each end bracket 174 also includes a circular slot 180 in a side of the end bracket 174 opposite from the tongue 178. The adjustable guide member 164 also includes a central support member 182 that has a circular arm 184 projecting laterally from each side thereof along an axis of rotation 186. Each circular arm 184 is snugly disposed within one of the circular slots 180. The central support member 182 may be attached proximate to the discharge end 101 of the flexible tube 98, e.g., by a press fit therearound as shown in FIG. 14, by an adhesive, by a fastener, or by any means of attachment known to one having skill in the art.

Figure 16:
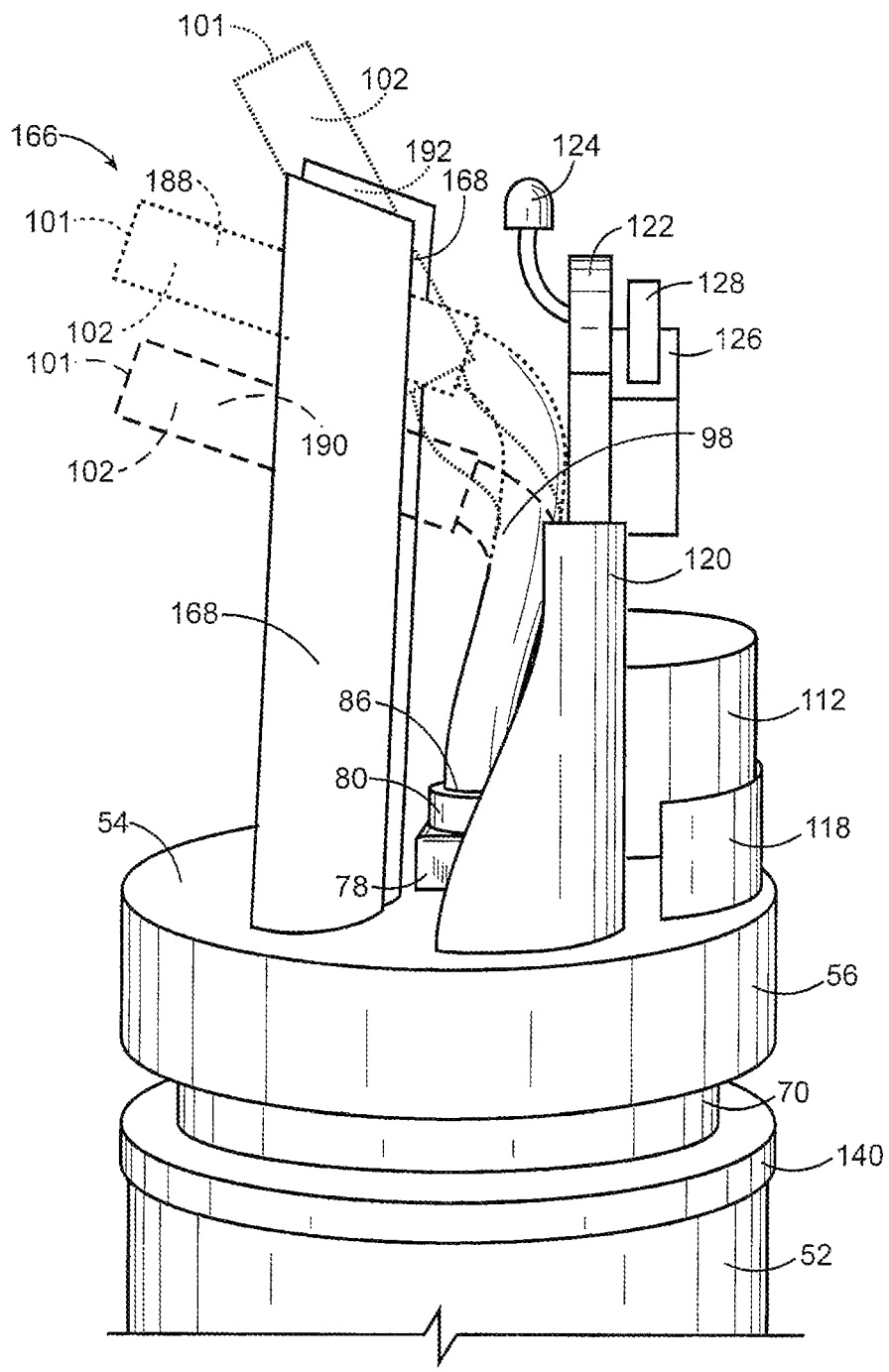
FIG. 16 is a right side isometric view of another embodiment of a volatile material dispenser including the adjustable guide member depicted in FIGS. 14 and 15.

The end brackets 174 may be slid up or down along the grooves 170 and the circular arms 184 may be rotatably adjusted within the circular slots 180. By such selective adjustment of the adjustable guide member 164, a user may select the orientation and/or the positioning of the discharge end 101 of the flexible tube 98 with respect to the container 52. As shown in FIG. 16, the adjustable guide member 164 allows the discharge end 101 of the flexible tube 98 to be fixedly held in a first position 188. The discharge end 101 of the flexible tube 98 may also be downwardly translated to be fixedly held in a second position 190 or may be upwardly translated and rotatably reoriented to be fixedly held in a third position 192. Indeed, the adjustable guide member 164 allows a user to select any combined rotational orientation and vertical position of the discharge end 101 of the flexible tube 98 about the axis 186 and along the grooves 170, respectively.

In a further embodiment, a volatile material dispenser similar to the embodiment shown in FIG. 16 includes a sensor (not shown) disposed on the platform 54 and facing radially away from the longitudinal axis 110. The sensor is in electronic communication with the printed circuit board 122 as will be further described in detail below. A housing 198 for the volatile material dispenser is shown in FIGS. 17 and 18. The housing 198 is generally similar to the housing 132 described hereinabove with regard to FIGS. 11 and 12 except for the following differences. A discharge orifice or slot 200 is disposed through the upper portion 138 and the medial portion 136 along the front side 150 of the housing 198. The housing 198 also includes an aperture 202 disposed through the front side 150 of the lower portion 134. When the housing 198 is mounted on the container 52 over the volatile material dispenser a sensor is disposed in the aperture 202 to allow sensing of the environment. Further, the discharge end 101 of the flexible tube 98 may be adjusted by the adjustable guide member 164 to be disposed anywhere within the slot 200.

In yet another embodiment, a volatile material dispenser similar to the embodiment shown in FIG. 16 includes a normally open switch (not shown) having a manual pushbutton or other mechanical actuator known to one having skill in the art mounted on a base. The normally open switch may be electronically connected to the printed circuit board 122 to trigger activation of the drive unit. Alternatively, the manual pushbutton may be mechanically linked to the discharge conduit 76 by a mechanical linkage known to one skilled in the art such that depression of the manual pushbutton radially displaces the tilt-activated valve stem 88. A depressible panel 214 on the back side 148 of the medial portion 136 of the housing 198, as shown in FIG. 18, may be adapted to contact and depress the manual pushbutton when the housing 198 is mounted to the container 52. The depressible panel 214 may be a living hinge or may be inwardly depressible in another way as known to one skilled in the art. The depressible panel 214 may also include a finger depression 216 to facilitate ease of use.

Figure 19:
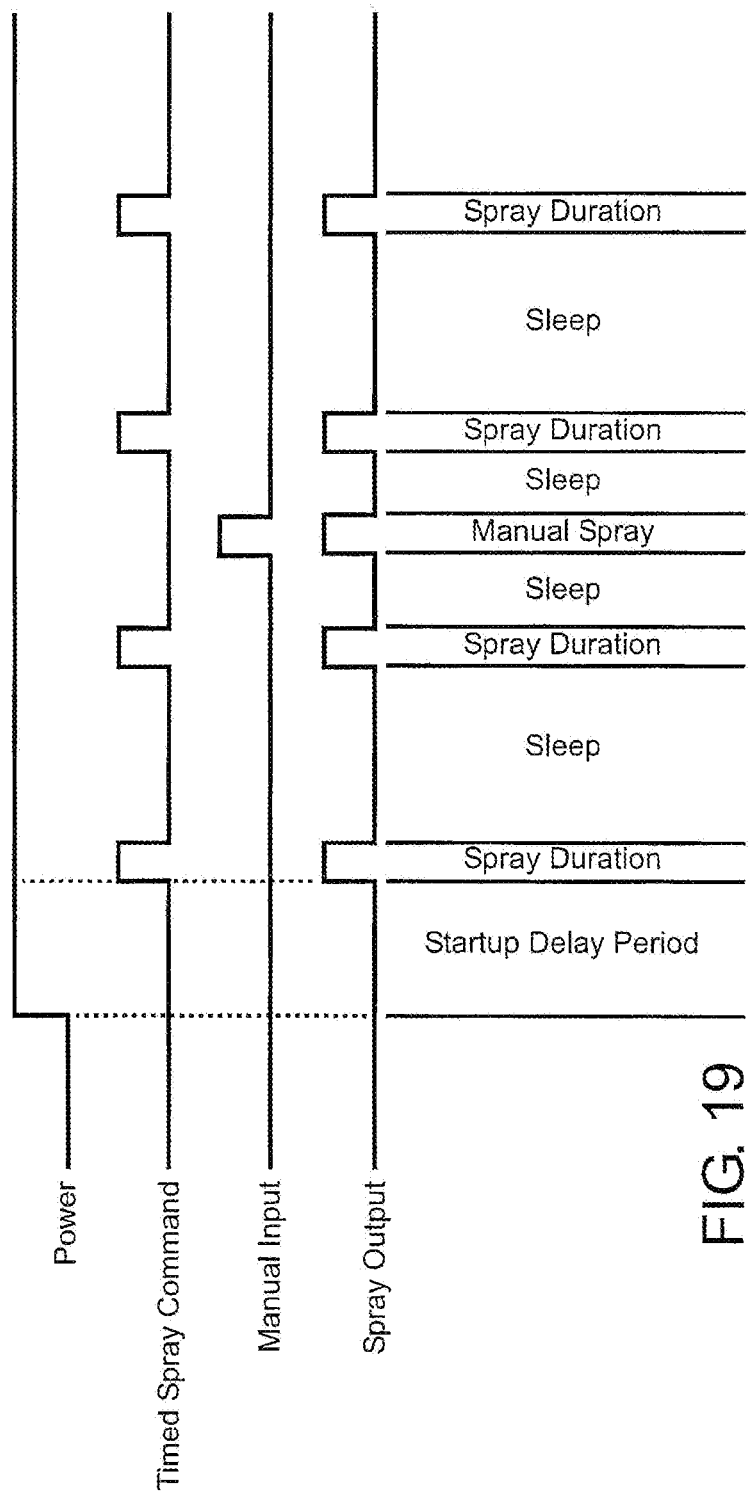
FIG. 19 is a timing diagram illustrating the operation of the volatile material dispensers of FIGS. 1-18 according to a first operational sequence.

FIG. 19 depicts a timing diagram that illustrates the operation of any of the volatile material dispensers hereinabove described during an in use condition. Initially, the volatile material dispenser, for example the volatile material dispenser 166, is energized by moving the positioning finger 128 of the linear switch assembly 126 from an "OFF" position 218 to one of four operating modes 220, 222, 224, and 226, as shown in FIG. 3, whereupon a control circuit (not shown), which may be etched on the printed circuit board 122, causes the volatile material dispenser 166 to enter a startup delay period. Each of the four operating modes 220, 222, 224, and 226 corresponds to a predetermined sleep period between consecutive spraying periods. For example, the first operating mode 220 may correspond to a five minute sleep period, the second operating mode 222 may correspond to a seven and a half minute sleep period, the third operating mode 224 may correspond to a fifteen minute sleep period, and the fourth operating mode 226 may correspond to a thirty minute sleep period. For the present example, we shall assume the first operating mode 220 has been chosen. Upon completion of the startup delay period, the solenoid assembly 112 is activated to discharge fluid from the container 52 during a first spraying period. The startup delay period is preferably about three seconds long, and the spraying period is typically about 98 milliseconds long. Upon completion of the first spraying period, the volatile material dispenser 166 enters a first sleep period that lasts 5 minutes. Upon expiration of the first sleep period the solenoid assembly 112 is activated to discharge fluid during a second spraying period. Thereafter, the volatile material dispenser 166 enters a second sleep period that lasts for 5 minutes. In the present example, the second sleep period is interrupted by the manual activation of the volatile material dispenser 166, whereupon fluid is dispensed during a third spraying period. Automatic operation thereafter continues with alternating sleep and spraying periods. At any time during a sleep period, the user may manually activate the volatile material dispenser 166 for a selectable or fixed period of time by depressing a manual pushbutton that may be mounted thereto as described above. Upon termination of the manual spraying operation, the volatile material dispenser 166 completes the pending sleep period. Thereafter, a spraying operation is undertaken.

In another embodiment, the linear switch assembly 126 may have a continuous range of settings instead of the four distinct operating modes 220, 222, 224, and 226 described above. In such an embodiment, the linear switch assembly 126 may be provided with a switch mechanism such as a dial (not shown), that provides for continuous user variation of the spraying period and/or the sleep period between continuous spray and sleep periods lasting several hours or days. In a further embodiment, the linear switch assembly 126 may be replaced and/or supplemented by a sensor, e.g., a photocell light sensor, which may be used as a motion detector. Alternatively, more than one sensor may be provided in lieu of the linear switch assembly 126 or in combination with same. It is anticipated that one skilled in the art may provide any type of sensor either alone or in combination with the linear switch assembly 126 and/or other sensors to meet the needs of a user. In one particular embodiment (not shown), e.g., the linear switch assembly 126 and a sensor are both provided in a volatile material dispenser. In such an embodiment, a user may choose to use the timer-based linear switch assembly 126 to automatically operate the solenoid assembly 112, or the user may choose to use the sensor to detect a given event prior to activating the solenoid assembly 112. Alternatively, such a volatile material dispenser may operate in a timer and sensor based mode of operation concurrently.

As noted above, the sensor may be a photocell light sensor. The photocell light sensor collects ambient light and allows the control circuit to detect any changes in the intensity thereof. Filtering of the photocell output is undertaken by the control circuit. If the control circuit determines that a threshold light condition has been reached, e.g., a predetermined level of change in light intensity, the control circuit develops a signal to activate the solenoid assembly 112. For example, if a volatile material dispenser including the photocell light sensor is placed in a lit bathroom, a person walking past the sensor may block a sufficient amount of ambient light from reaching the sensor to cause the control circuit to activate the solenoid assembly 112 and discharge a fluid. Further, other motion detectors known to those of skill in the art may also be utilized, e.g., a passive infrared or pyro-electric motion sensor, an infrared reflective motion sensor, an ultrasonic motion sensor, or a radar or microwave radio motion sensor.

The LED 124 is illuminated when the volatile material dispenser 166 is in an operative state. The LED 124 blinks intermittently once every fifteen seconds during the sleep period. Depending on the selected operating mode, the blinking frequency of the LED 124 begins to increase as a spraying period becomes imminent. The more frequent illumination of the LED 124 serves as a visual indication that the volatile material dispenser 166 is about to discharge fluid contents into the atmosphere.

Any of the embodiments described herein may be modified to include any of the structures or methodologies disclosed in connection with different embodiments. Further, the present disclosure is not limited to aerosol containers of the type specifically shown. Still further, the volatile material dispensers of any of the embodiments disclosed herein may be modified to work with any type of fluid container having a tilt-activated valve stem.

INDUSTRIAL APPLICABILITY

Aerosol dispensers are commonly used to dispense volatile materials such as air fresheners, deodorants, insecticides, germicides, decongestants, perfumes, and the like, that are stored within aerosol containers. Automated valve activation systems for aerosol containers allow the contents thereof to be released without human interaction, for example, according to a predetermined time schedule. Tilt-activated valve stems for aerosol container release valves typically require less force to operate than vertically activated valve stems, but may lack precise directional control. A system for automatically activating a tilt-activated valve stem providing selective directional control is presented. The system may be installed in a typical overcap for use with ordinary tilt-activated aerosol containers, resulting in an improvement in utility of the aerosol container.

Numerous modifications will be apparent to those skilled in the art in view of the foregoing description. Accordingly, this description is to be construed as illustrative only and is presented for the purpose of enabling those skilled in the art to make and use what is herein disclosed and to teach the best mode of carrying out same. All patents, patent applications, and other references cited herein are incorporated herein by reference as if they appear in this document in their entirety. The exclusive rights to all modifications which come within the scope of this disclosure are reserved.

We claim:

1. A volatile material dispenser, comprising:
   a drive unit for use with a container, wherein the drive unit is to be activated in response to a signal from at least one of a timer, a sensor, or a manual actuator to radially displace a tilt-activated valve stem of the container;
   a housing, the drive unit disposed within the housing; and
   a flexible tube having a discharge end disposed within the housing and fixedly held with respect to the container, wherein the flexible tube is adapted to be in fluid communication with the tilt-activated valve stem.

2. The volatile material dispenser of claim 1 further including a switch assembly that provides one or more operating modes for the timer.

3. The volatile material dispenser of claim 1, wherein the sensor is a photocell light sensor.

4. The volatile material dispenser of claim 1, wherein the sensor is an ultrasonic motion sensor.

5. The volatile material dispenser of claim 1, wherein the sensor is a microwave radio motion sensor.

6. The volatile material dispenser of claim 1 further including the container having the tilt-activated valve stem.

* * * * *